US008982195B2

(12) United States Patent
Claus et al.

(10) Patent No.: US 8,982,195 B2
(45) Date of Patent: Mar. 17, 2015

(54) DIGITAL VIDEO CAPTURE SYSTEM AND METHOD WITH CUSTOMIZABLE GRAPHICAL OVERLAY

(75) Inventors: Michael J. Claus, Newport Coast, CA (US); Alex Urich, Santa Rancho Margarita, CA (US); Paul W. Rockley, Corona Del Mar, CA (US)

(73) Assignee: Abbott Medical Optics Inc., Santa Ana, CA (US)

( * ) Notice: Subject to any disclaimer, the term of this patent is extended or adjusted under 35 U.S.C. 154(b) by 1220 days.

(21) Appl. No.: 11/953,229

(22) Filed: Dec. 10, 2007

(65) Prior Publication Data

US 2008/0316304 A1 Dec. 25, 2008

Related U.S. Application Data

(63) Continuation-in-part of application No. 11/851,572, filed on Sep. 7, 2007.

(60) Provisional application No. 60/824,896, filed on Sep. 7, 2006.

(51) Int. Cl.
 *G06Q 50/22* (2012.01)
 *G06F 19/00* (2011.01)
(52) U.S. Cl.
 CPC .................................. *G06F 19/3406* (2013.01)
 USPC ................... 348/54; 348/65; 348/45; 348/46; 348/72; 348/211.4
(58) Field of Classification Search
 CPC . G06F 19/3418; G06F 19/3406; G06Q 50/22; G06Q 50/24
 USPC ...................................................... 348/54, 65
 See application file for complete search history.

(56) References Cited

U.S. PATENT DOCUMENTS

| 5,454,722 A | 10/1995 | Holland et al. |
| 6,397,286 B1 | 5/2002 | Chatenever et al. |
| 6,629,948 B2 | 10/2003 | Rockley et al. |
| 7,400,752 B2 | 7/2008 | Zacharias |
| 2001/0029029 A1* | 10/2001 | Gombrich et al. ........... 435/40.5 |
| 2003/0159141 A1* | 8/2003 | Zacharias ....................... 725/37 |
| 2003/0176774 A1* | 9/2003 | Hickle et al. .................. 600/300 |
| 2006/0010040 A1* | 1/2006 | Kerr, II ........................... 705/22 |
| 2006/0050144 A1* | 3/2006 | Kennedy ......................... 348/65 |
| 2007/0223574 A1* | 9/2007 | Roman et al. ............ 375/240.01 |
| 2007/0236514 A1* | 10/2007 | Agusanto et al. ............. 345/646 |
| 2007/0238981 A1* | 10/2007 | Zhu et al. ...................... 600/424 |

FOREIGN PATENT DOCUMENTS

| EP | 1712210 A1 | 10/2006 |
| WO | WO2006/060423 A1 | 6/2006 |

* cited by examiner

*Primary Examiner* — Djenane Bayard
(74) *Attorney, Agent, or Firm* — Abbott Medical Optics Inc.

(57) ABSTRACT

A method and system for acquiring and transmitting video image data with parameter data superimposed thereon is provided. The design includes an input device configured to receive said video image data and separately receiving said parameter data, the input device configured to transmit the video image data and parameter data as separate data streams. The design further includes a computing device comprising a computer based utility configured to receive the separate data streams, store the separate data streams, edit at least one data stream, and generate combined video data. Combined video data represents combined video image data and parameter data. The design also includes a display device configured to present the combined video data.

22 Claims, 9 Drawing Sheets

DIGITAL VIDEO CAPTURE SYSTEM AND METHOD WITH CUSTOMIZABLE GRAPHICAL OVERLAY

This application is a continuation-in-part of co-pending U.S. patent application Ser. No. 11/851,572, filed Sep. 7, 2007, which claims priority based on U.S. Provisional Patent Application Ser. No. 60/824,896, filed Sep. 7, 2006, which are both incorporated herein by reference.

BACKGROUND OF THE INVENTION

1. Field of the Invention

The present design relates generally to the art of medical instrument systems, and more specifically to a method and apparatus for collecting and replaying video recordings of surgeons performing medical procedures with a simultaneous rendering of the medical instrument operating parameters.

2. Description of the Related Art

Many surgeons record each surgical procedure they perform. Recording typically involves a digital video capture and data storage system that allows surgeons to record images during the course of the surgical procedure as generated by a camera mounted on, for example, a surgical microscope. Surgeons rarely, if ever, separately record other parameters or events generated during the procedure.

When playing back such recordings, viewers are typically limited to the raw video footage recorded and no other information. For example, during an ophthalmic surgery, the procedures performed on the eye are the only images visible. The problem with such a situation is that subsequent viewers have no idea what challenges were encountered—the surgeon must be present and inform the viewers, or the viewer must review notes from the procedure, or the viewer is totally left in the dark as to what occurred during the procedure. For example, if a sudden drop in pressure occurred in a suction instrument, the viewer has no idea this occurred. Similarly, settings for instruments and dynamic parameters, particularly those that change rapidly or dramatically from initial settings, are not available and it is rare that detailed notes are available, such as "18 minutes, 22 seconds into the procedure—changed power settings from high to low."

Based on the foregoing, it would be advantageous to provide for simultaneous replay of camera video images with other parameters pertinent to the procedure, rendered on a single video monitor display device for use in medical instrument systems that overcomes the foregoing drawbacks present in previously known designs.

SUMMARY OF THE INVENTION

According to a first aspect of the present design, there is provided a system for acquiring and transmitting video image data with parameter data superimposed thereon is provided. The design includes an input device configured to receive said video image data and separately receiving said parameter data, the input device configured to transmit the video image data and parameter data as separate data streams. The design further includes a computing device comprising a computer based utility configured to receive the separate data streams, store the separate data streams, edit at least one data stream, and generate combined video data. Combined video data represents combined video image data and parameter data. The design also includes a display device configured to present the combined video data.

According to a second aspect of the present design, there is provided a method for displaying video image data of a procedure, such as a medical procedure. The method includes receiving a first set of data including a visual representation of the procedure, receiving a second set of data including parameter data, such as medical instrument data, associated with the procedure, the second set of data being separate from the first set of data. The method also includes combining the first set of data with the second set of data by overlaying the second set of data on the first set of data.

These and other advantages of the present design will become apparent to those skilled in the art from the following detailed description of the design and the accompanying drawings.

BRIEF DESCRIPTION OF THE DRAWINGS

The present design is illustrated by way of example, and not by way of limitation, in the figures of the accompanying drawings in which.

DETAILED DESCRIPTION OF THE INVENTION

The following description and the drawings illustrate specific embodiments sufficiently to enable those skilled in the art to practice the system and method described. Other embodiments may incorporate structural, logical, process and other changes. Examples merely typify possible variations. Individual components and functions are generally optional unless explicitly required, and the sequence of operations may vary. Portions and features of some embodiments may be included in or substituted for those of others.

General

As noted, current designs do not allow a viewer to employ or view certain parameters or information, such as medical instrument operating parameters, together with recorded images simultaneously on one video monitor display device. Concurrent presentation of recorded images and key operational parameters can increase the user's appreciation for specific surgical tasks by increasing the information value or knowledge content of the recording. Such a recording may be more useful to the viewer if a representation of operating parameters and settings encountered during the procedure. In the case of a phacoemulsification ophthalmic procedure, recording and subsequent real time playback of parameters including but not limited to vacuum, power, flow, and foot pedal position generated by the medical instrument, can be highly useful when viewing the surgical procedure after it has been completed.

At best, previous surgical recording procedures may entail use of two independent systems, one supporting the video image data stream and one supporting the medical instrument parameter data stream. Each system's associated video monitor display device may be arranged in a side-by-side configuration suitable for simultaneous viewing. In this arrangement, the first systems display device can render the camera image data stream and the second systems display device can render instrument parameter data. Such a design requires the user to view two separate display devices during replay. In order to ascertain the instrument parameter settings at a point in the camera video image presentation, the user must shift her focus from the camera video image display device to the instrument settings display device. Requiring the user to move their focus back and forth between two independent display devices sufficient to observe a particular step in the surgical procedure can be problematic and may require the user to replay a certain surgical procedure step a number of times to appreciate both the camera video data and the instrument parameter data, thus making it extremely difficult to observe and determine the actual instrument setting at the desired procedure step.

Further, synchronization of two separate recording systems is difficult at best and impossible at worst. It is difficult for users to operate two independent recording systems during a complex surgical procedure such as removal of a cataract. For example, the user responsible for operating the two independent systems must synchronize the video data stream with the instrument parameter data stream in order to achieve an acceptable simultaneous rendering via the two display devices during replay. The user can synchronize the dual data streams by manually operating one of the independent systems to either advance or delay the data stream in relation to the other data stream in time to align the two data streams. Aligning the data streams to synchronize the simultaneous presentation of instrument parameters and camera images is complex to operate, time-consuming to implement, and requires comprehensive training to master.

Furthermore, in order to move the presentation, by either advancing forward or reversing backward in time, for example in the backward direction to repeat part of the procedure already viewed, the user must manually operate each independent system to locate the desired time. In this arrangement, simply moving the replay of the two data streams in time is subject to the same issues discussed above and therefore prone to error.

In addition, today's designs do not afford a practical method for stepping through the video data stream on a frame-by-frame basis while simultaneously progressing through instrument parameter data stream. Today's designs are further limited because they do not allow the user to readily edit the presentation of a surgical procedure, for example to shorten the length of a recorded procedure to fit into a desired time allotment. Editing involves the user performing a complex set of tasks on each system in order to accurately and precisely edit each data stream in time to produce the desired length or content.

These limitations result in creating an often difficult, if not impossible, task for the user to replay, edit, and view video image data captured from a surgical camera in conjunction with observing the surgical instrument operating parameter data.

Present Design

The present design is directed to providing customizable graphical video overlays superimposed over surgical procedure video recordings captured and recorded by a safety critical system such as a medical instrument system, for example a phacoemulsification/vitrectomy surgical system.

The present design may allow for playback, editing, and archive functionality for recordings, and enable the user to analyze each surgical video, stepping through on a frame-by-frame basis, to show or hide instrument parameter data. The present design enhances the educational usefulness of replaying surgical procedure videos as a teaching tool. Users may choose to show data parameters including but not limited to aspiration, vacuum, power, bottle height, and occlusion settings.

The design provides a quick, easy to use, accurate, and reliable video capture and image processing system for replay of surgical videos with instrument data represented by data plots, animated images, and plain text. The present design may allow users to manipulate data previews in a variety of ways, for example enlarge a graph or move the data to a different area of the screen, so the overlay data does not block the user from viewing key or desirable portions of the surgical footage. In addition, the present design may allow the user play, copy, move, or delete a recorded video and may facilitate performing these actions on both the video and companion instrument file.

The present design provides an accurate presentation of actual instrument parameter data, in real-time as data plots, animated images, plain text, or static images, in conjunction with the surgical video and may enable users to more directly compare and contrast the video of a surgical procedure relative to the conduct of the same or similar procedure.

In short, the present design may allow a user to recall previous recordings and view instrument data and settings even if they were not displayed to the surgeon or staff during surgery. In general, any type of system or software application configured to view or replay video frames, for example an image processing application, may benefit from the design presented herein. While discussed with respect to a phacoemulsification system such a design is not limited to a phacoemulsification system, surgical system, or even a medical system. The present design may be implemented in, for example, systems including but not limited to phacoemulsification-vitrectomy systems, vitrectomy systems, surgical systems, dental systems, industrial applications, and aerospace applications.

The present design may employ various interface mechanisms to control the presentation of the surgical video with instrument data as a graphical video overlay on a video display device connected to the surgical system or medical instrument, such as via a cathode ray tube or liquid crystal display, monitor device, or other subsystem.

The design is discussed herein with a particular emphasis on simultaneous replay of camera video image frames synchronized with instrument parameter settings rendered on a single video monitor display device for use in medical instrument systems as stored in and replayed from the surgical systems video storage device.

The present design may include a mechanical user interface button panel configured to control operations such as record, play, bookmark and stop. In addition, the present design may include a graphical user interface to further control video operations and may include editing functionality and may provide the ability to hide or show instrument data.

The present design is intended to provide a reliable, noninvasive, and efficient digital video capture system for use in viewing a surgical procedure video and real-time instrument parameter settings simultaneously on a single display device.

Again, the present design is discussed herein with a particular emphasis on a medical or hospital environment, where a surgeon or health care practitioner performs. For example, one embodiment of the present design is in or with a phacoemulsification/vitrectomy surgical system that comprises an independent graphical user interface (GUI) host module, an instrument host module, a GUI device, and a controller module, such as a foot switch, to control the surgical system.

Figure 1:
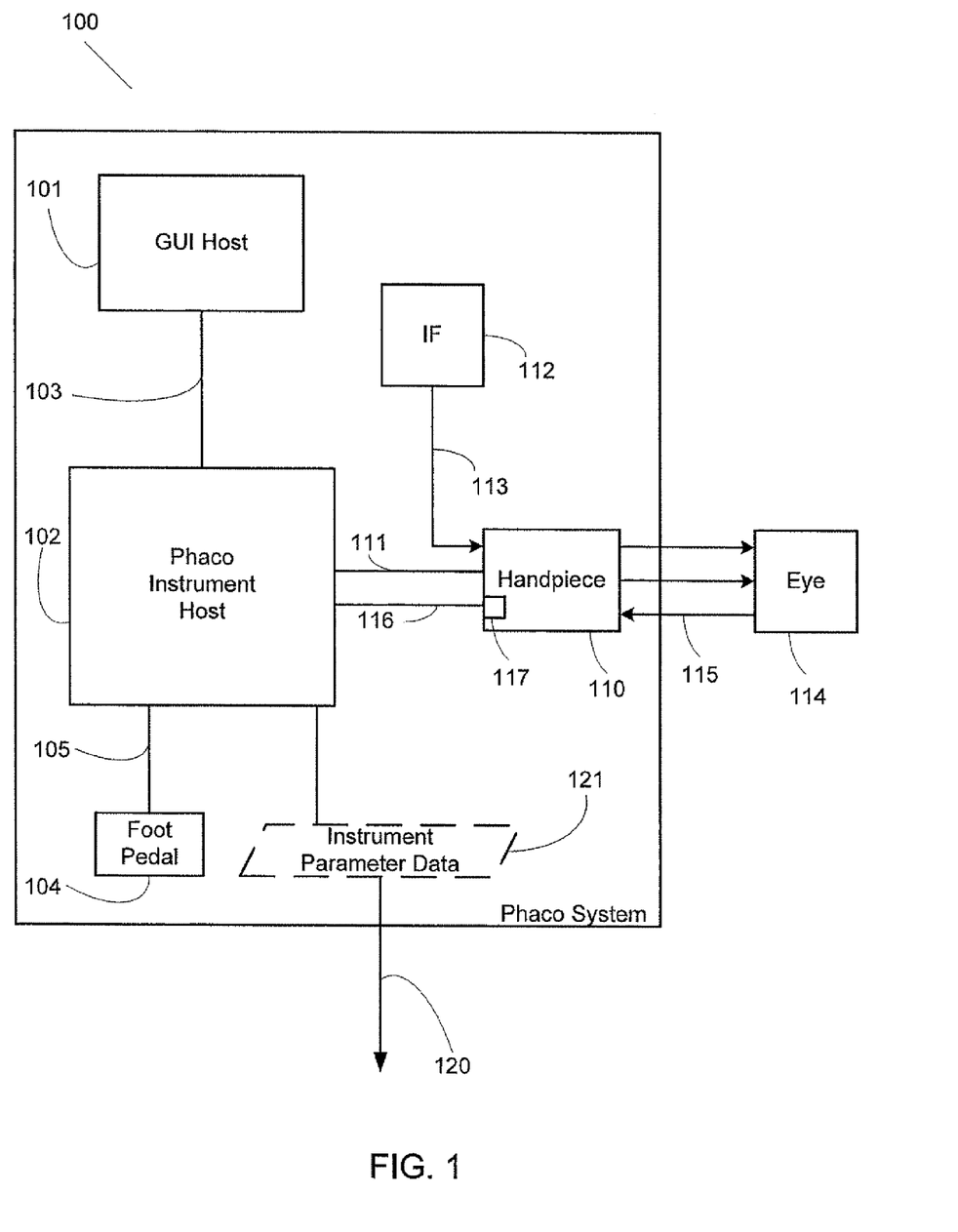
FIG. 1 is a functional block diagram of a phacoemulsification system that may be employed in accordance with an aspect of the present design.

FIG. 1 illustrates an exemplary phacoemulsification/vitrectomy system 100 in a functional block diagram to show the components and interfaces for a safety critical medical instrument system that may be employed in accordance with an aspect of the present design. A serial communication cable 103 connects GUI host 101 module and Phaco instrument host 102 module for the purposes of controlling Phaco instrument host 102 by GUI host 101. Phaco instrument host 102 may be considered a computational device in the arrangement shown, but other arrangements are possible. An interface communications cable 120 is connected to instrument host 102 module for distributing instrument parameter data 121 to other systems, subsystems and modules within and external to instrument host 102 module. Examples of instrument parameter data 121 may include vacuum, power, flow, and foot pedal position generated from phacoemulsification instrument host 102 during the surgical procedure. Although shown connected to the phaco instrument host 102 module, interface communications cable 120 may be connected or realized on any other subsystem (not shown) that could accommodate such an interface device able to distribute instrument parameter data 121.

A foot pedal switch 104 module may transmit control signals relating internal physical and virtual switch position information as input to instrument host 102 over serial communications cable 105. Instrument host 102 may provide a database file system for storing configuration parameter values, programs, and other data, such as surgeons name, saved in a storage device (not shown). In addition, the database file system may be realized on the GUI host 101 or any other subsystem (not shown) that could accommodate such a file system.

The phacoemulsification/vitrectomy system 100 has a handpiece 110 that includes a needle and electrical driving hardware, typically a piezoelectric crystal, for ultrasonically vibrating the needle. The instrument host 102 supplies power on line 111 to a phacoemulsification/vitrectomy handpiece 110. An irrigation fluid source 112 can be fluidly coupled to handpiece 110 through line 113. The irrigation fluid and ultrasonic power are applied by handpiece 110 to a patient's eye, or affected area or region, indicated diagrammatically by block 114. Alternatively, the irrigation source may be routed to eye 114 through a separate pathway independent of the handpiece. Aspiration is provided to eye 114 by the instrument host 102 pump (not shown), such as a peristaltic pump, through lines 115 and 116. A switch 117 disposed on the handpiece 110 may be utilized to enable a surgeon/operator to select an amplitude of electrical pulses to the handpiece via the instrument host and GUI host. Any suitable input device, such as for example, a foot pedal switch 104 may be utilized in lieu of switch 117.

Figure 2:
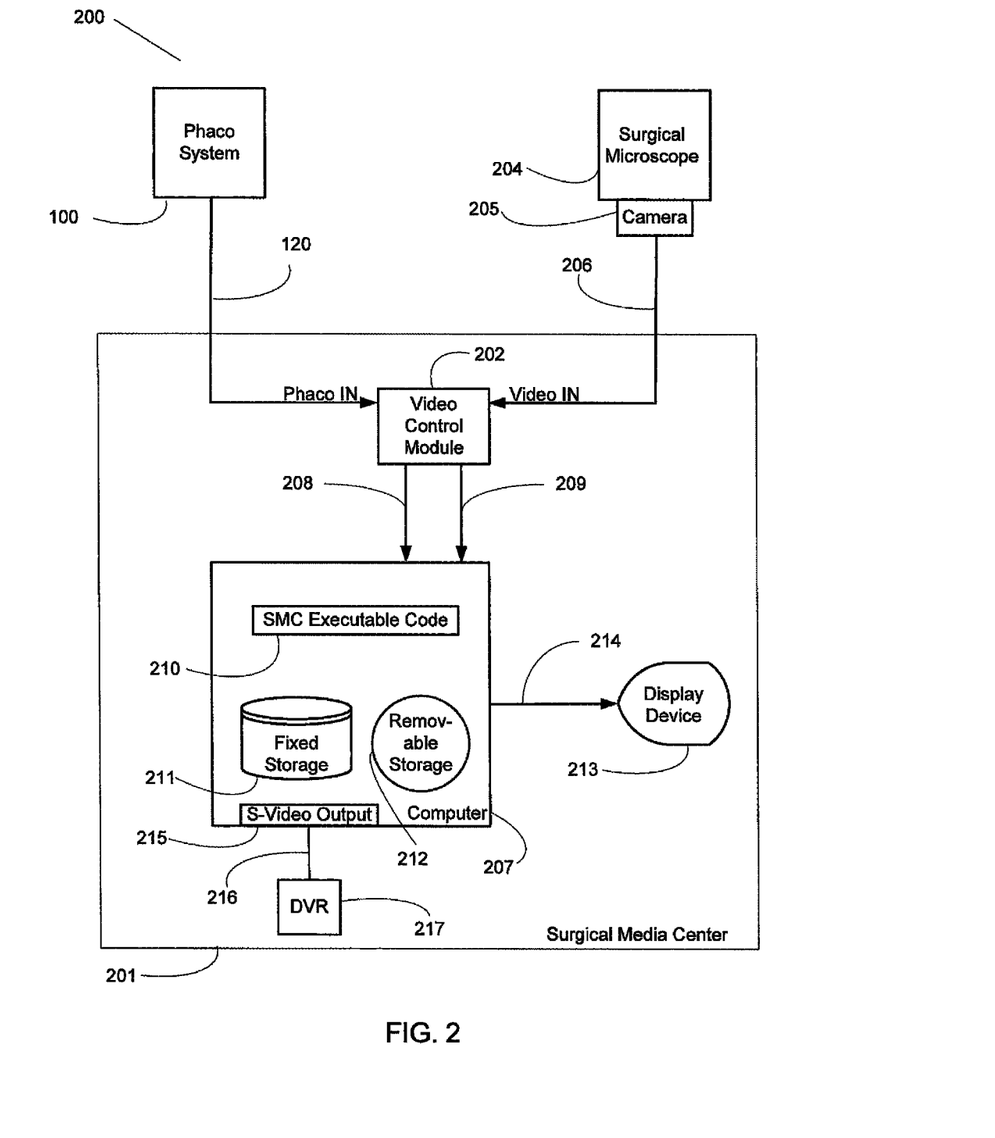
FIG. 2 is a functional block diagram of a surgical media center system that may be employed in accordance with an aspect of the present design.

FIG. 2 illustrates and exemplary surgical system 200 in a functional block diagram to show the components and interfaces for a surgical media center image processing system 201 for recording and playback of surgical procedures and instrument parameter data 121 in accordance with an aspect of the present design. Surgical system 200 may include a medical instrument, such as the phacoemulsification/vitrectomy system 100 shown in FIG. 1. Communications cable 120, for example a serial cable, may connect phacoemulsification/vitrectomy system 100 to SMC image processing system 201, shown as Phaco IN, via video control module (VCM) 202. The surgical system 200 may further include a surgical microscope 204 focused on the surgical procedure, e.g. patients eye, and may employ camera 205 or other device suitable for video capture. Surgical system 200 may transfer the resulting video data, analog, digital, or both, to SMC image processing system 201, shown as Video IN, via VCM 202. A video composite cable 206, for example provisioned with RCA connectors, or an S-Video cable may connect VCM 202 and camera 205 for the purposes of transferring the video data stream.

SMC image processing system 201 is an image processing system that manages the video data captured by camera 205 as well as the instrument parameter data 121 in real-time. Managing video and instrument parameter data may include operations such as record, playback, edit, preview and bookmark. Examples of video data supported by the present design may include national television system committee (NTSC), phase alternating line (PAL), high definition television (HDTV), séquentiel couleur à mémoire (SECAM), or other video format suitable for image capture by camera 205. Examples of instrument parameter data supported by the present design may include, but are not limited to, vacuum, power, flow, and foot pedal position, or other data generated from phacoemulsification/vitrectomy system 100 during the surgical procedure.

VCM 202 may connect to a serial port (not shown) provided by computer 207 via communications cable 208, such as a serial cable, sufficient to provide phaco instrument parameter data 121 for storage. Concurrently, VCM 202 may connect to a Universal Serial Bus (USB) port (not shown) provided by computer 207 via communications cable 209, such as a USB video cable, sufficient to provide video data for storage. Use of USB technology may provide power to VCM 202 from computer 207 USB port. Optionally, a digital video recorder (DVR) 217, video cassette recorder (VCR), television, and other storage or display device may be connected to computer 207 S-Video Output 215 port via S-Video cable 216.

Computer 207 may be considered a computational device in the arrangement shown, but other processing arrangements may be employed. Computer 207 is a processing device and may include but is not limited to hardware, software, firmware, a personal computer, or other processing environment suitable for executing surgical media center (SMC) executable code 210. In the configuration as shown in FIG. 2, computer 207 may provide storage such as fixed storage 211 and removable storage 210 (e.g. optical read/write drives such as digital versatile disc optical drive and compact disc).

SMC functionality may be realized by computer 207 operating SMC executable code 210. SMC storage devices 211 and 212 may be configured to store the video data stream originating from camera 205. The present design may be configured to store the received video data stream as analog video, digital video, digital data, or any combination thereof.

SMC functionality may involve managing the multimedia data, i.e. video data stream, and may perform synchronizing the temporal relationship between the instrument parameters and settings data stream from phacoemulsification/vitrectomy system 100 and the video data steam from surgical microscope 204. The SMC image processing system 201 may display the camera video data stream in combination with the corresponding parameters and instrument settings at each instant during the procedure, typically as a graphical video overlay, presented at display device 213 connected to SMC image processing system 201 via display cable 214. Display device 213 may be an integral part of computer 207, a separate display device, e.g. remote, such as attaching a video monitor to an available S-Video Output realized in computer 207, or both.

During playback, the present design may allow the user to show or hide different elements of the graphical video overlay, i.e. relaying instrument data, rendered on video display device 213. Elements of the graphical video overlay may include, for example, data plots, animated images, plain text, and static images. The present design may employ data plots to represent real-time activity such as aspiration, vacuum, and power utilized during surgery. The present design may involve animated images such as bar graphs or speedometer style graphs to represent real-time activity and plain text may be employed to show elements including but not limited to real time values, phaco instrument mode, and surgeon name. The present design may support static images that may be custom tailored by the user. For example, the user may want to add a logo, picture, or text for presentation during a portion or all of the playback.

In this arrangement, surgical system 200 may record a video image of the surgical procedure and record instrument parameters and settings utilized by phacoemulsification/vitrectomy system 100 in real-time. SMC image processing system 201 may synchronize instrument parameter data 121 stream with the video stream data allowing simultaneous display of video stream data with a graphical overlay showing the corresponding parameters and system settings at each instant of the procedure on a frame-by-frame basis. This cumulative data, i.e. the video data and instrument data may be stored and archived in fixed storage device 211, such as read only memory (RAM) and disc memory, e.g. a hard-drive. In addition the present design may store and archive the cumulative data in a removable storage device 212, for example a DVD or CD writer, memory stick, or other portable storage device suitable for providing the removable storage device functionality.

Surgical Media Center (SMC) Construction and Operation

The present design may involve a surgical media center system configured to record and playback surgical procedures and separately receive, record and overlay the phacoemulsification/vitrectomy instrument activity for simultaneous viewing on a single display device. The SMC of the present design configures and controls the presentation of surgical video with instrument data presented as a graphical video overlay on top of a video image during playback, herein described within an image processing safety critical medical instrument/surgical system.

Figure 3:
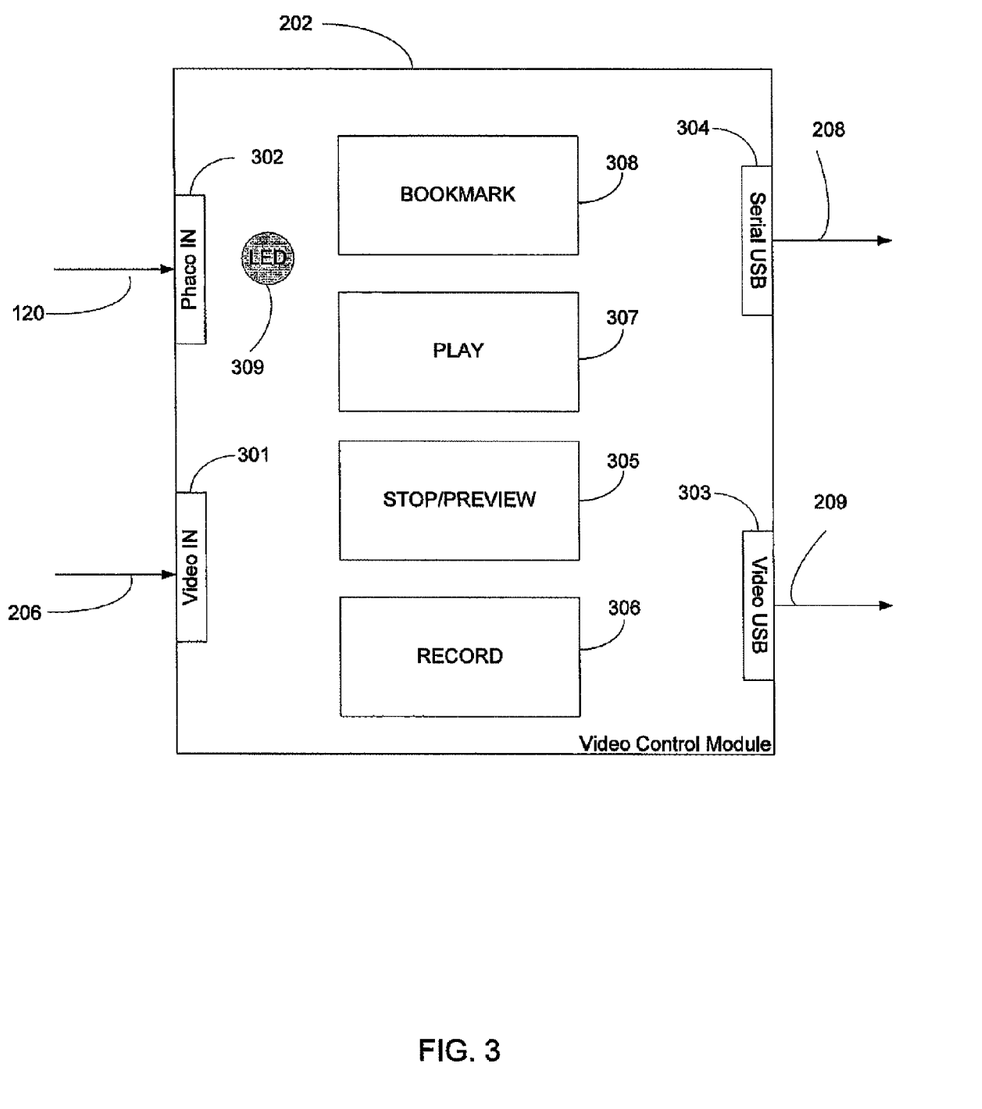
FIG. 3 is a diagram of an exemplary video control module illustrating input and output configuration and switch selector functionality that may be employed in accordance with an aspect of the present design.
Figure 4:
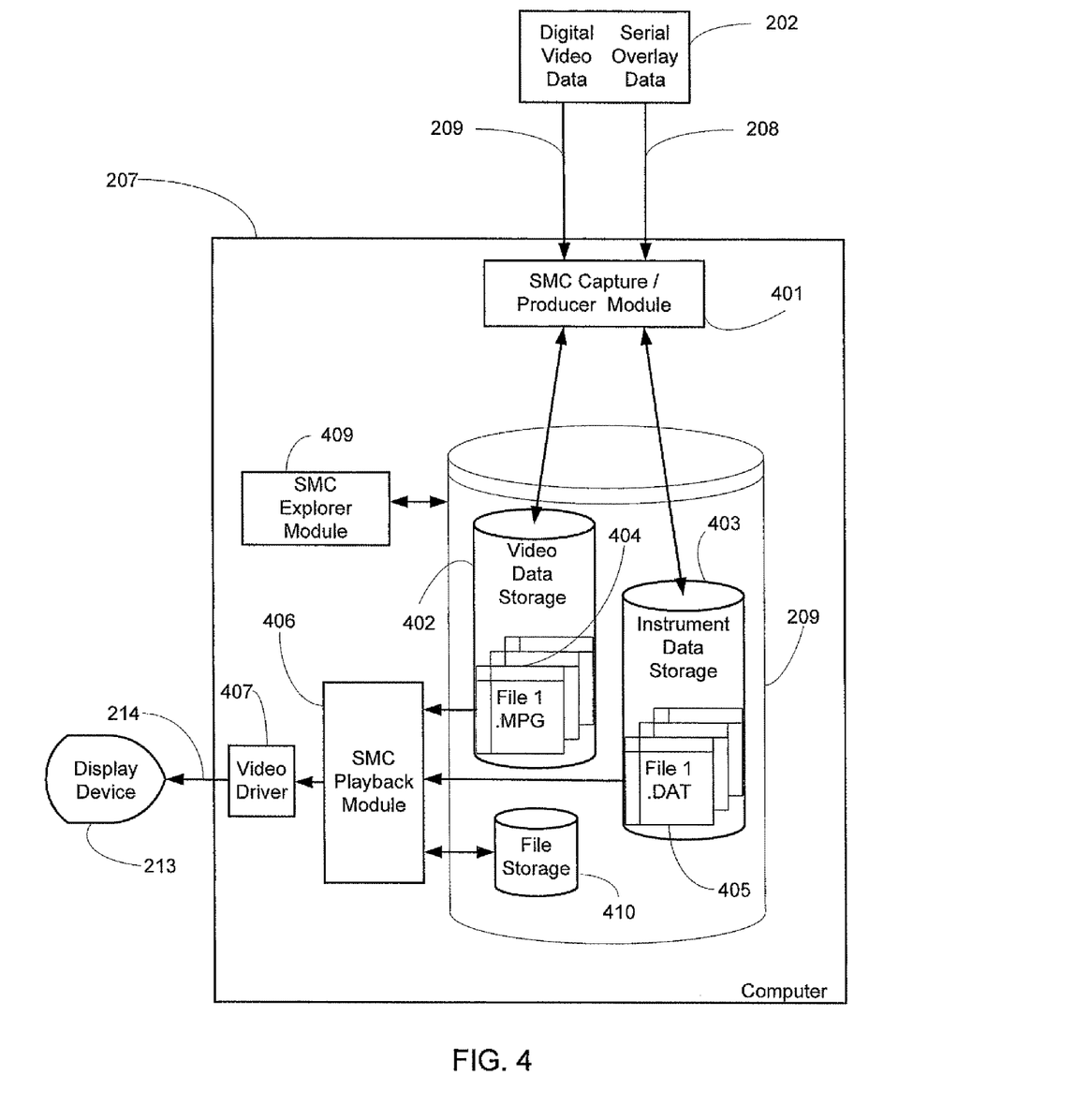
FIG. 4 is a functional block diagram of an exemplary computer operating surgical media center executable code to realize record and playback functionality that may be employed in accordance with an aspect of the present design.

The SMC system may include a video control module, a computer executing the SMC application software, and a display device configured as illustrated in FIG. 2. FIGS. 3 and 4 provide further details for the construction of a general SMC system such as is illustrated in FIG. 2. FIG. 3 illustrates the video control module electrical interface configuration as a single hardware module having user interface selector switch functionality. FIG. 4 illustrates an exemplary computer operating surgical media center executable code to realize the present designs record and playback functionality.

FIG. 3 illustrates an exemplary video control module (VCM) 202 where the VCM functionality is realized in standalone hardware configured to convert the video camera data stream into universal serial bus (USB) format, and convert the phacoemulsification/vitrectomy system 100 data stream, e.g. phaco data, to USB format. Such conversion to USB format is generally known to those skilled in the art. VCM 202 may receive the video camera data stream via communications cable 206 at Video IN 301, and may receive instrument parameter data 121 stream via communications cable 120 at Phaco IN 302. After conversion to USE format, VCM 202 may transmit the Video USE data at Video USB 303 via communications cable 209, and transmit the instrument data at Serial USE 304 via communications cable 208 to computer 207 (not shown). In addition, VCM 202 may provide isolation from computer 207 such that if the functionality is not desired, is damaged or functioning improperly, the procedure can progress without video and parameters being recorded by disconnecting the VCM 202 from computer 207.

Conversion in the device shown in FIG. 3 is from a video standard to a USB video standard, while instrument parameters or data are converted from serial format to serial USB. Conversion in this manner and between these formats is generally known to those skilled in the computing arts. Conversion hardware or software performing this functionality is present in VCM 202. Note that two separate channels are maintained through the VCM 202, one for instrument data and parameters and one for video data or video image data, and the VCM 202 in general does not mix these two signals.

VCM 202 may additionally provide an external user interface arranged to control the operation of SMC image processing system 201. The external interface may provide access to major functional features and functions such as Stop/Preview, Record, Playback, and Bookmark.

Software functionality of the SMC and VCM 202 will now be described, and these functions and software for providing the functions recited are generally understood by those skilled in the computing and/or video recording arts. As may be appreciated, certain software functionality may be provided on the SMC, VCM 202, computer 207, monitor, or any other device configured to provide the functionality recited herein, including providing software functionality on more than one device. Certain functionality may be provided in hardware or firmware.

"Stop/Preview" selects the SMC preview operational mode. In the Preview mode, the present design may display the surgical video provided from camera 205 without recording the video data stream. To enable the Preview mode, the user may select the VCM 202 Stop/Preview button 305 or may use computer 207 pointing device to 'click-on' and select Preview from the SMC menu bar (not shown) on display device 213 presented by SMC executable code 210 operating within computer 207. Pointing devices may include but are not limited to a touch screen monitor, trackball, mouse touchpad, keypad, and foot pedal switch. Effectuating this functionality is generally known to those skilled in the digital photography arts and/or the computing arts.

"Record" selects the SMC record operational mode. In the record mode, the present design typically initiates recording and storage of the surgical video data stream provided by camera 205 by saving a MPG file onto either fixed or removable storage. To enable the record mode, the user may select the VCM 202 Record button 306. The record mode may also be initiated via the SMC menu bar. If the phacoemulsification/vitrectomy system 100 is connected to VCM 202 or a device performing similar functions, the present design may record the graphical overlay data, i.e. instrument data 121 stream, concurrently with the surgical video data by saving a file, such as a .DAT file, onto either fixed or removable storage. VCM 202 may flash a Light Emitting Diode 309 (LED) to indicate phaco instrument data is present and detected. If VCM 202 detects phaco instrument data, the SMC may provide for display the overlay data concurrent with the video data or combined display of the data.

To stop a recording, the user may select the Stop/Preview button 305 on VCM 202 or via the SMC menu bar. The present design may allow recording to be initiated and terminated from phacoemulsification/vitrectomy system 100, VCM 202 button panel, or the SMC menu bar generated by an SMC Graphical User Interface (GUI) displayed on computer 207 display device or an externally attached display device, e.g. remote viewing outside the operating theater. The present design is configured such that the VCM has priority over phacoemulsification/vitrectomy system 100 when initiating or terminating a recording and in this arrangement the present design will ignore commands sent from phacoemulsification/vitrectomy system 100.

"Play" selects the SMC Playback operational mode. The present design may allow the user to playback recorded SMC files with or without the video overlay. To enable the Play mode, the user may select VCM 202 Play button 307 to replay or playback the last recorded file. The play mode may also be initiated via the SMC menu bar to playback other previously saved files. Referring to FIG. 4, when the play mode is accessed from the SMC menu bar, the present design may open a SMC Explorer 409 to playbacks recorded files. The present design may allow the user to perform file management operations including but not limited to play, copy, move, or delete a recorded video. SMC Explorer 409 may perform file management operations by acting on the video and the companion overlay data files according to the operation selected. In Play mode, the present design may render a software toolbar to the video, for example located at the top or the bottom of the video presentation. The toolbar may provide incremental steps to speed up or slow down the playback. The present design may allow the user to hide or make the toolbar visible. SMC image processing system 201 may also provide other toolbar functionality such as pan, zoom, increase or decrease contrast, and sharpen the rendered image, again generally understood by those skilled in the art of computing devices and/or video recording.

"Bookmark" selects the SMC bookmark operational mode. Bookmarks may appear as vertical lines on the scroll bar presented by the SMC GUI. The scroll bar functionality provided by the present design system and method may allow forward and backward scrolling through the video. The present design may allow the user to hide or make the scroll bar visible. Users may navigate between bookmarks, for example by using the caret keys (<>) on a keyboard attached to computer 207, to go forward or backwards. The present design may allow the user to automatically or manually rewind and repeat the video within two bookmarks. In the bookmark mode, the present design may allow the user to place a position marker in the video during recording or playback of a file. During recording the user may set one or more bookmarks by pressing Bookmark button 308 on the VCM panel.

FIG. 4 illustrates a functional block diagram for a SMC system 400 including the present designs apparatus and method wherein SMC modules execute within computer 207 to realize the SMC functionality. In this arrangement, the present design is configured to superimpose a graphical data overlay on a surgical video for use in determining the phaco instrument host 102 operating parameter data and settings during replay.

FIG. 4 illustrates an exemplary computer 207, such as a personal computer, configured to interface with VCM 202 and operate SMC executable code 210 where the record, edit, and playback functionality is realized and presented on display device 213. Computer 207 may receive the digital video data stream via communications cable 209 where a SMC capture/producer module 401 may control writing the data to video data storage 402. The present design may write the video data as a file, such as an MPEG file named Filex.MPG as shown at 404. In addition, computer 207 may receive the serial overlay data stream via communications cable 208 where a SMC capture/producer module 401 may control writing the data to instrument data storage 403. The present design may write the overlay data as data file, here named Filex.DAT as shown at 405. The file name Filex.* is for illustrative purpose only. The present design may be configured to receive the surgeons name from the phaco instrument and name the SMC files .MPG and .DAT files accordingly, e.g. surgeons-name.MPG and surgeons-name.DAT. If the surgeon's name was not specified in the phaco instrument, the present design may utilize a default name.

The present design's SMC playback module 406 may read data for playback from video data storage 402 and synchronize in time the video data and overlay data simultaneously and provide the data to computer 207 native video driver 407. Video driver 407 may send video information to display device 213 over display cable 214 for presentation of a composite image representing both data formats, i.e. .MPG and .DAT. SMC playback module 406 may be configured to combine the video and overlay in one video file r e.g. MPEG-2 and store this file in file storage 410. The playback module 406 may require the user to enter a name for the combined file.

The present design's method for combining may involve re-recording the video file with the overlay data added. In this arrangement, the time to create a combined file will equal the total elapsed time of the video file. The present design may generate combined files that equal MPEG-2 DVD presentation quality. The SMC files saved in file storage 410 may be recalled and replayed by playback module 406 on display device 213. Methods for generating a graphical video overlay and superimposing the overlay onto a video frame, image, or stream are generally understood by those skilled in the art.

The SMC system 400 illustrated in FIG. 4 may operate separate from instrument host 102 or may be configured to operate as part of phaco instrument 201 or any other subsystem, for example surgical microscope 202 and surgical media center 204 or be realized using external devices and/or software. The SMC utility functionality may be realized in hardware, software, firmware, or any combination of processing thereof. In addition, the present design may be realized by embedding the SMC executable code 210 in an existing medical instrument system design. Although FIG. 4 illustrates the system 400 Playback 406, Capture/Producer 401, and Explorer 409 as separate entities, i.e. module, process, and mechanism, the present design is not limited to a set number of entities and may be realized by incorporating some or all of the functionality of the present design into a single software unit or entity.

Figure 5:
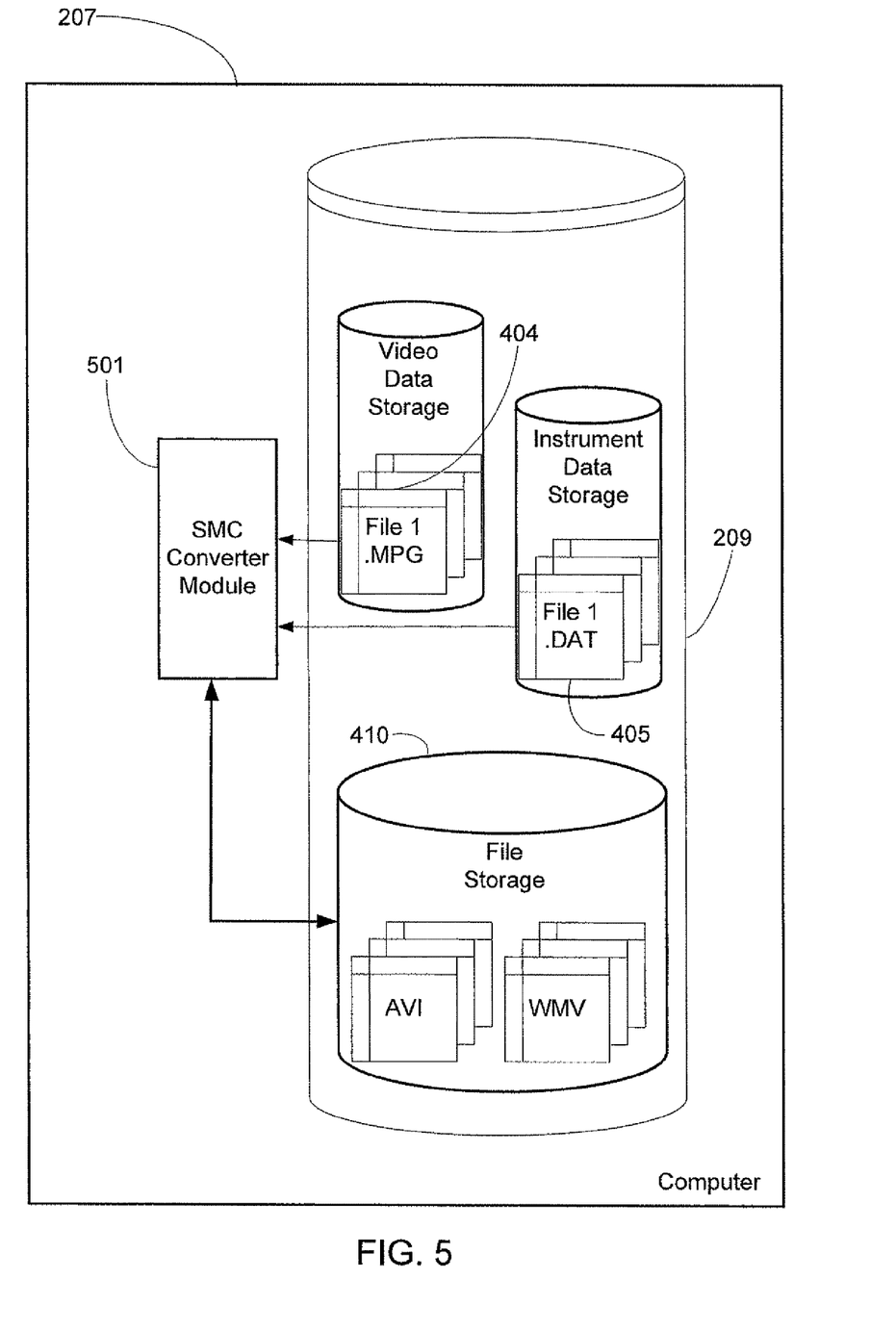
FIG. 5 is a functional block diagram of an exemplary computer operating surgical media center executable code to realize file conversion functionality that may be employed in accordance with an aspect of the present design.

FIG. 5 is a functional block diagram of an exemplary computer 207 operating surgical media center executable code to realize file conversion functionality. The present design may allow the user to reprocess the combined SMC file. Reprocessing the combined files may employ SMC converter module 501. Converter module 501 may retrieve saved SMC files and translate from the MPEG-2 format to other media formats, e.g. Windows Media (WMV/ASF), QuickTime (Apple(MPEG-4)), AVI and other media formats and save these media formats in file storage 410. During reprocessing, the converter module 501 may be arranged to reduce the file size and may allow the user to select a lower bit rate. Converter module 501 may be configured to split a file into smaller files, where the user may assert the start and end times of the split or merge two or more files into one file, e.g. ASF. In addition, converter module 501 may enable the user to slow a video segment (i.e. slow motion) by selecting a time magnification value.

SMC Video Overlay

SMC files are combinations of two files, where one file stores or maintains the video data and the second file stores or maintains the video overlay information. These files can be combined and played together using SMC system 201. The present design may allow the user to change the entire overlay after the surgical procedure video recording has finished, i.e. independently. In addition, when replayed the data plots presented by the overlay may provide the current data in conjunction with past and future data over a period of time.

Figure 6:
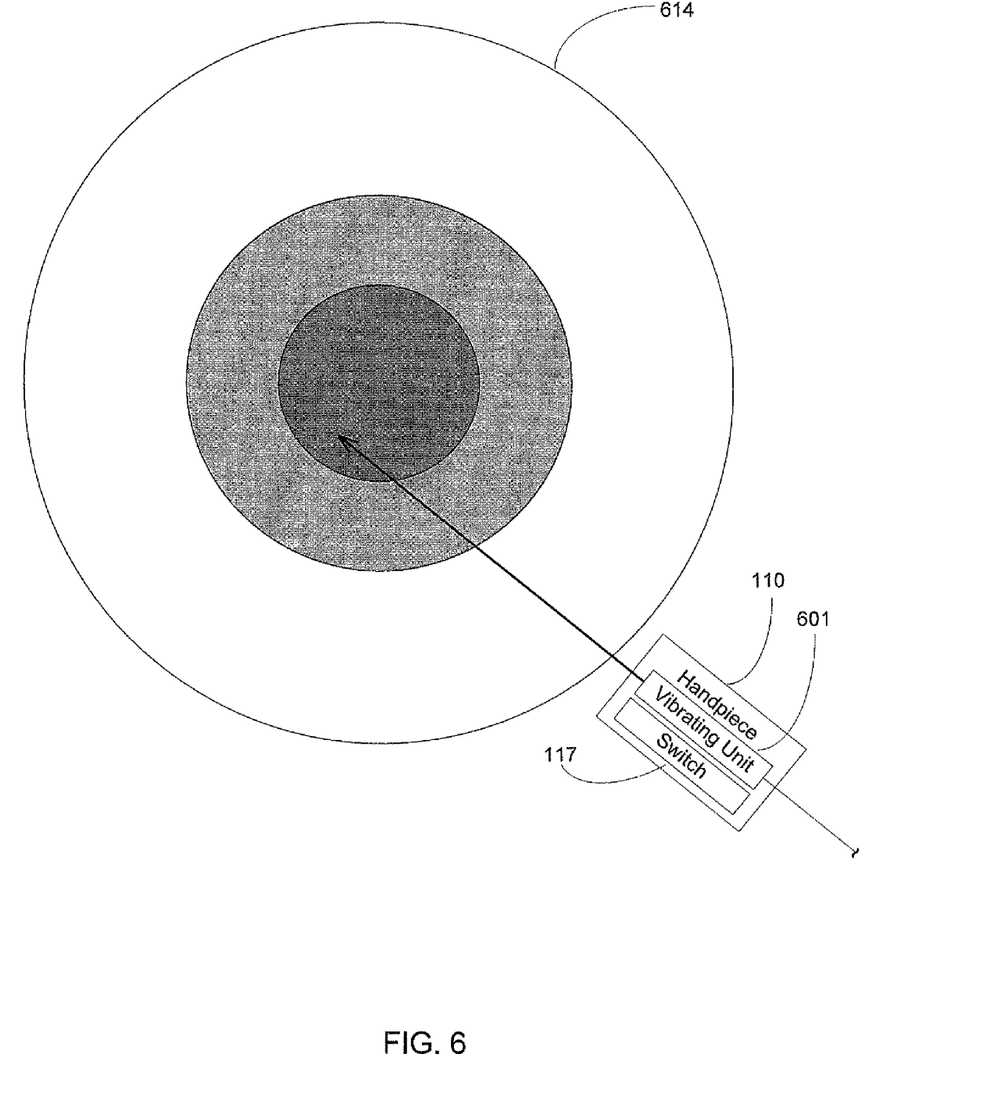
FIG. 6 is a diagram illustrating an example video screen generated by the present design, without instrument parameters, as rendered on video display device for viewing by a user in accordance with an aspect of the present design.

FIG. 6 illustrates an example video screen generated by the present design, without instrument parameters, as rendered on video display device for viewing by a user in accordance with an aspect of the present design.

FIGS. 6 through 8B provide diagrammatic representations of example video screens generated by the SMC system available for viewing by the user when operating the present design's playback functionality. For purposes of illustration, handpiece 110 including vibrating unit 601 and switch 117, is shown in FIG. 6 through FIG. 8B as it may be recorded with eye 614 during the surgical procedure.

Figure 7:
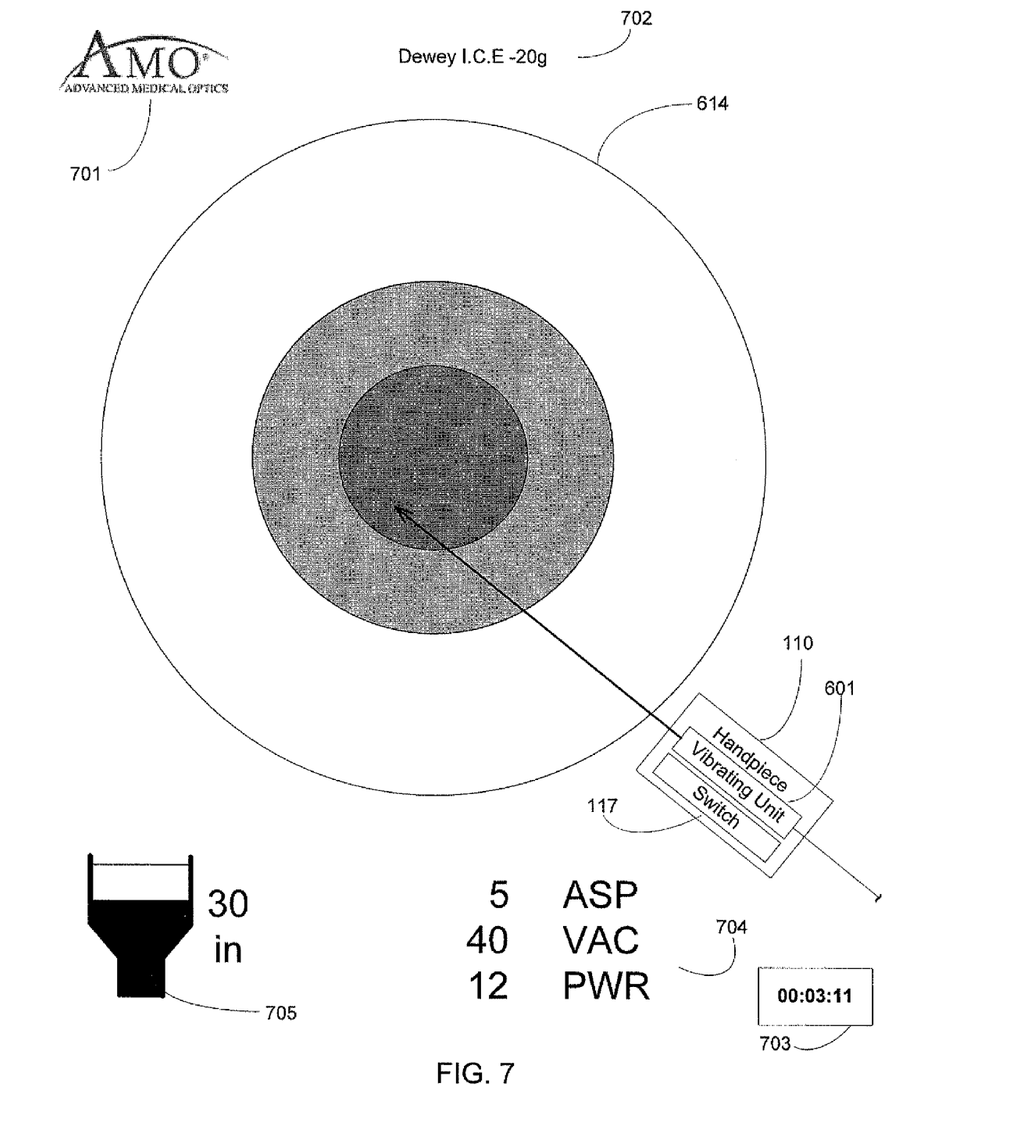
FIG. 7 is an example video screen illustrating sample screen customization features including icons, logos, surgeons name, and text display of instrument parameters as rendered on a video display device for viewing by a user in accordance with an aspect of the present design.

The present design may enable users to create customized overlays. Customization may include but is not limited to adding, moving, and removing elements. Elements may include but are not limited to data plots, animated images, plain text, or static images. FIG. 7 is an example video screen illustrating screen customization features including the display plain text and static images. For example the user may desire to display their corporate logo at 701 a static image. Static images may allow the user to add logos, pictures, comments, and other information to the video overlay. In addition the user may desire to display the surgeon's name at 702, clock at 703, and the actual parameter data values at 704 as plain text customization are shown in FIG. 7. The elements may be positioned at any location within a video frame as rendered on a video display device.

Figure 8A:
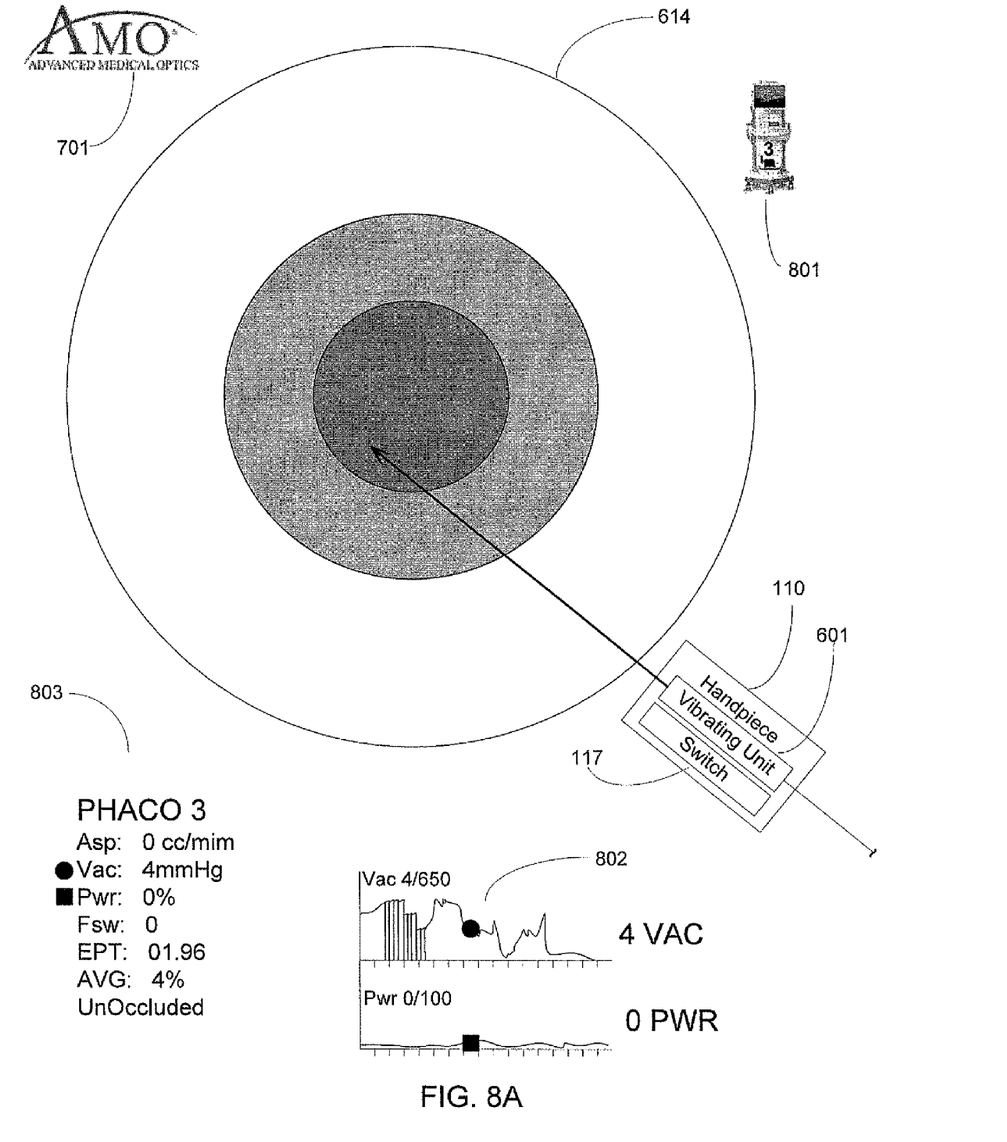
FIG. 8A is an example video screen illustrating sample screen customization features including real time linear graphs displaying instrument parameter data as rendered on a video display device for viewing by a user in accordance with an aspect of the present design.

FIG. 8A is an example video screen illustrating sample screen customization features including real time linear graphs displaying instrument parameter data as rendered on a video display device for viewing by a user, and includes a display of plain text, data plots, and static images. As one example, a user may wish to display an icon representing the medical instrument at 801 as a static image. The user may desire to display the current instrument parameter data in conjunction with past and future data over a period of time. Vacuum and power settings over a period of time are displayed as a data plot at 802. In addition, real-time parameter data is rendered as plain text at 803.

Figure 8B:
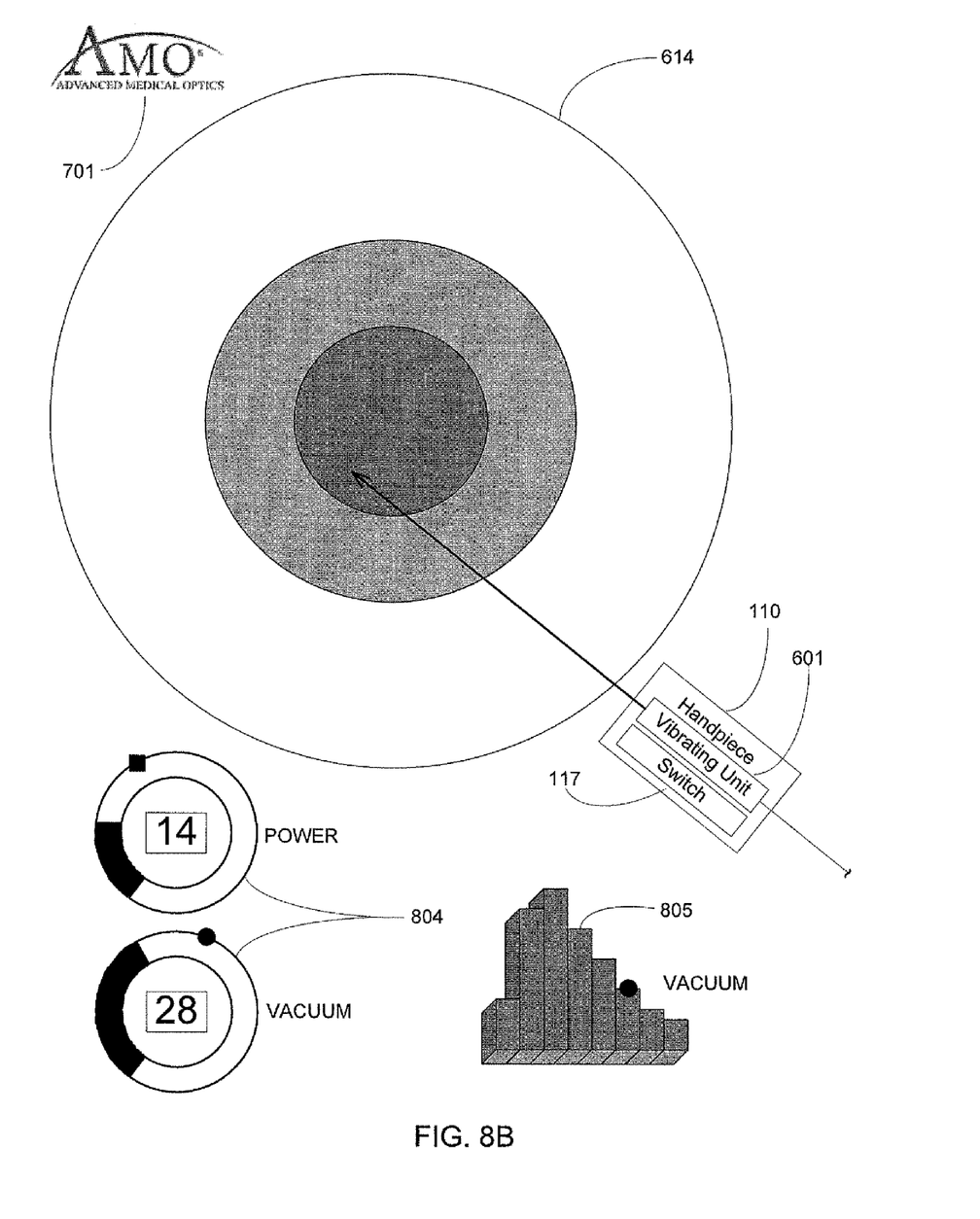
FIG. 8B is an example video screen illustrating sample screen customization features including real time circular graphs displaying instrument parameter data as rendered on a video display device for viewing by a user in accordance with an aspect of the present design.

FIG. 8B is an example video screen illustrating sample screen customization features including real time circular graphs displaying instrument parameter data as rendered on a video display device for viewing by a user in accordance with an aspect of the present design. FIG. 8B is an example video screen illustrating screen customization features involving animated images. For example the user may desire to display a power and a vacuum speedometer at 804 separate animated images. The user may desire to display the current instrument parameter data in conjunction with past and future data over a period of time. Vacuum settings over a period of time are displayed as an animated image at 802.

Operation of surgical system 200 assumes that the user, e.g. surgeon, previously performed a surgical procedure that was recorded by SMC system 201 and the data, i.e. the video image of the surgery and the parameters employed by the phacoemulsification system during the surgery, are saved in fixed or removable storage and ready for playback. During playback of the stored data, the user may configure and control the SMC system 201 to render the overlay data at a desired position for presentation on a video display device in association with, or superimposed on, or on top of the stored data presented, i.e. surgical procedure video, typically by using drag and drop or positional placement software functionality for a specific software module, such as desiring the aspiration pressure to be displayed in the upper right corner of the screen at position 155 horizontal, 0 vertical.

A user operating the surgical system may provide input to the SMC system to configure and control how the elements are displayed via a touch screen, trackball, mouse or other pointing device, or keyboard. For example, configuration may include choosing the measurement unit, e.g. metric or English, setting the start and stop time of the segment, pan and zoom to enlarge a portion of the video displayed, adjusting the surgical video contrast and sharpen the image, and saving the overlay.

As may be appreciated from FIGS. 6 through 8B, SMC system 201 may enable the present design to place the customization features at any location on the screen on the video image during rendered during playback and allow the user to move or hide individual features. The user may reposition, expand or compress each customization feature to avoid masking an important part of the surgical video image.

The design presented herein and the specific aspects illustrated are meant not to be limiting, but may include alternate components while still incorporating the teachings and benefits of the design. While the design has thus been described in connection with specific embodiments thereof, it will be understood that the design is capable of further modifications. This application is intended to cover any variations, uses or adaptations of the design following, in general, the principles of the design, and including such departures from the present disclosure as come within known and customary practice within the art to which the design pertains.

The foregoing description of specific embodiments reveals the general nature of the disclosure sufficiently that others can, by applying current knowledge, readily modify and/or adapt the system and method for various applications without departing from the general concept. Therefore, such adaptations and modifications are within the meaning and range of equivalents of the disclosed embodiments. The phraseology or terminology employed herein is for the purpose of description and not of limitation.

What is claimed is:

1. A method for displaying video image data of a medical procedure, comprising:

receiving a first set of data comprising a visual representation of the medical procedure;

receiving a second set of data comprising medical instrument data readings obtained during the medical procedure, said second set of data being separate from said first set of data;

selecting a subset of the medical instrument data readings from the second set of data; and enabling a user to create an overlay comprising a customization feature visually representing the subset of the medical instrument data readings, wherein the overlay is superimposed on the first set of data;

wherein enabling the user to create the overlay comprises allowing the user to selectively position and size the customization feature at a desired location within the overlay, and wherein the customization feature comprises textual medical instrument data readings and non-textual medical instrument data readings made over a period of time.

2. The method of claim 1, wherein enabling the user to create the overlay comprises enabling the user to establish at least one overlay element and position said overlay element in juxtaposition with the visual representation.

3. The method of claim 2, wherein said overlay element comprises at least one from a group comprising a data plot, an animated image, plain text, and a static image.

4. The method of claim 1, wherein said overlay superimposed on the first set of data yields the video image data, the method further comprising providing the video image data to a visual display.

5. The method of claim 1, wherein the first set of data comprises a visual recording of a surgical procedure.

6. The method of claim 1, wherein medical instrument data readings comprise medical instrument related data generated during the visual recording of a surgical procedure.

7. The method of claim 1, wherein receiving the first set of data and receiving the second set of data occur at the same time.

8. A computer processing system configured to provide video image data with instrument data readings superimposed thereon, comprising:

an input device configured to receive said video image data and separately receive said instrument data readings, the input device configured to transmit the video image data and instrument data readings as separate data streams;

a computing device comprising a computer based utility configured to receive the separate data streams, select data to be displayed from the instrument data readings, and enable a user to create an overlay comprising a customization feature visually representing the selected data to be displayed from the instrument data readings, wherein the overlay is superimposed on the video image data to form combined video data, wherein enabling the user to create the overlay comprises allowing the user to selectively position and size the customization feature at a desired location within the overlay, and wherein the customization feature comprises textual instrument data readings and non-textual instrument data readings made over a period of time; and a display device configured to present the combined video data.

9. The system of claim 8, wherein said computing device comprises a personal computer connected to the input device.

10. The system of claim 8, wherein said input device may receive analog video as a separate data stream from digital video.

11. The system of claim 8, wherein the digital video stream is stored on the computing device as an MPEG file.

12. The system of claim 8, wherein each data stream is stored on the computing device as a DATA file.

13. The system of claim 8, wherein the computing device is further configured to edit the combined video data, wherein editing comprises altering selected segments of the combined video data.

14. A method for displaying video image data of a procedure, comprising:

receiving a first set of data comprising a visual representation of the procedure;

receiving a second set of data comprising instrument data readings obtained during the procedure, said second set of data being separate from said first set of data;

selecting a subset of the instrument data readings from the second set of data; and enabling a user to create an overlay comprising a customization feature visually representing the subset of the instrument data readings, wherein the overlay is superimposed on the first set of data;

wherein enabling the user to create the overlay comprises allowing the user to selectively position and size the customization feature at a desired location within the overlay, and wherein the customization feature comprises textual instrument data readings and non-textual instrument data readings made over a period of time.

15. The method of claim 14, wherein the procedure comprises a medical procedure.

16. The method of claim 14, wherein the overlay comprises at least one overlay element selectively positioned in juxtaposition with the visual representation.

17. The method of claim 16, wherein said at least one overlay element comprises at least one from a group comprising a data plot, an animated image, plain text, and a static image.

18. The method of claim 14, wherein said overlay being superimposed on the first set of data yields the video image data, the method further comprising providing the video image data to a visual display.

19. The method of claim 14, wherein the first set of data comprises a visual recording of a surgical procedure.

20. The method of claim 14, wherein medical instrument data readings comprise instrument related data generated during the visual recording of a surgical procedure.

21. The method of claim 14, wherein receiving the first set of data and receiving the second set of data occur at the same time.

22. A computer processing system for use in association with a medical procedure, the computer processing system configured to acquire and provide video image data with medical instrument data readings superimposed thereon, the computer processing system comprising:

an input device configured to receive said video image data of the medical procedure and separately receiving said medical instrument data readings obtained during the medical procedure, the input device configured to convert and transmit the video image data and medical instrument data readings as separate medical procedure data streams;

a computing device comprising a computer based utility configured to receive the separate medical procedure data streams, select data to be displayed from the medical instrument data readings, and enable a user to create an overlay comprising a customization feature visually representing the selected data to be displayed from the medical instrument data readings, wherein the overlay is superimposed on the video image data to form combined medical procedure video data, wherein enabling the usr to create the overlay comprises allowing the user to selectively position and size the customization feature at a desired location within the overlay, and wherein the customization feature comprises textual medical instrument data readings and non-textual medical instrument data readings made over a period of time; and a display device configured to present the combined medical procedure video data.

* * * * *